United States Patent [19]

Mashberg

[11] 4,321,251

[45] Mar. 23, 1982

[54] DETECTION OF MALIGNANT LESIONS OF THE ORAL CAVITY UTILIZING TOLUIDINE BLUE RINSE

[75] Inventor: Arthur Mashberg, East Orange, N.J.

[73] Assignee: The United States of America as represented by the Department of Health and Human Services, Washington, D.C.

[21] Appl. No.: 105,079

[22] Filed: Dec. 19, 1979

[51] Int. Cl.$^3$ .................. A61K 6/00; G01N 1/30; G01N 33/48

[52] U.S. Cl. ............................ 424/3; 424/7; 424/9; 424/49

[58] Field of Search ............... 424/3, 7, 9, 49

[56] References Cited

FOREIGN PATENT DOCUMENTS 2628468 12/1976 Fed. Rep. of Germany .......... 424/3

OTHER PUBLICATIONS

Strong, Arch. Otolaryng, vol. 87, May 1968, pp. 101–105.
Niebel, J. Amer. Dent. Assoc., vol. 68, 1964, pp. 801–806.
Shedd, Amer. J. Surg., vol. 110, 1965, pp. 631–634.
Shedd, Arch. Surg., vol. 95, 1967, pp. 16–22.
Vaughan, Otolaryng, Clin. of NA, vol. 5, 1972, pp. 301–302.
Ross, "Notes & Comments," Dental Abs., vol. 13, 1968, p. 453.
Mashberg, Cancer, Pub. pending.
Benveniste, Chem. Abs., vol. 86, 1977, Ab. No. 86:102805j.

*Primary Examiner*—Anna P. Fagelson
*Attorney, Agent, or Firm*—John S. Roberts, Jr.

[57] ABSTRACT

A method of clinical diagnosis and a composition for detecting malignant lesions of the oral cavity by utilizing as a rinse, toluidine blue preferably in acetic solution of water and ethanol. A preferred rinse is 5 cc 1% toluidine blue solution which is utilized in 1% acetic acid and water. In the method the solution (5–10 cc) is poured into floor of mouth and patient is advised to rinse and gargle.

1 Claim, No Drawings

DETECTION OF MALIGNANT LESIONS OF THE ORAL CAVITY UTILIZING TOLUIDINE BLUE RINSE

The present invention involves the use of toluidine blue

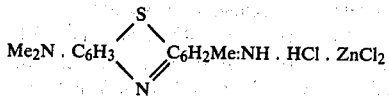

a basic metachromatic nuclear stain which stains nuclear material of malignant lesions but not normal mucosa, has been established as a useful modality for identifying malignant changes of the squamous mucosa. Its application is a simple, fast and inexpensive technique. One difficulty previously with the use of toluidine blue as a detecting agent has been some false negatives (underdiagnosis) as well as many false positives (overdiagnosis) and this difficulty has been found where toluidine blue was applied or applied in a neutral solution.

PRIOR ART STATEMENT

Strong, M. S., Vaughan, C. W., Incze, J. S. "Toluidine blue in the management of carcinoma of the oral cavity", *Arch. Otolaryng*, 87: 527–531, 1968.

Niebel, H. H., and Chomet, B. "In vivo staining test for delineation of oral intra-epithelial neoplastic change," *J. Amer. Dent. Assoc.*, 68: 801–806, 1964.

Shedd, D. P., Hukill, P. B., and Bahn, S. "In vivo staining properties of oral carcinoma," *Amer. J. Surg.*, 110: 631–634, 1965.

Shedd, D. P., Hukill, P. B., Bahn, S., et al. "Further appraisal of in vivo staining properties of oral cancer," *Arch. Surg.*, 95: 16–22, 1967.

Vaughan, C. W. "Supravital staining for early diagnosis of carcinoma," *Otolaryng. Clinics of North America*, 5: 301–302, June 1972.

Ross, W. L. "Notes and comments," *Dental Abstracts*, 13: 453, 1968.

Mashberg, A. "Toluidine blue application as a diagnostic adjunct in the detection of asymptomatic oral squamous carcinoma," Publication pending in Cancer.

In an attempt to decrease false positives, a study was designed with a 10–14 day waiting period after lesion recognition to allow inflammatory or other non-neoplastic lesions to resolve after withdrawal of any known etiologic agent before applying toluidine blue. This reduced false positives. A preferred method of clinical use is to utilize a rinse at Day 1 and if an area of stain is detected then select one day from Day 10 to Day 14 for an application to the detected area.

The results of the test indicate an average of a false negative rate of 6.9% and false positive rate of 6.8%. It is believed that the 10–14 day waiting period is sufficient to reduce false positives. These percentages are compared with a simple clinical rate of 4.8% false negative and 28.5% false positive, or overdiagnosis.

An advantageous use of the toluidine rinse was discovery of second primary cancers in the mouth or pharynx which were missed on clinical examination but were identified when the stain flowed into areas adjacent to or at a distance from the primary lesion. Application of stain indiscriminately to high risk areas resulted in the discovery of unobserved lesions.

The present invention is devoted to the development of a toluidine blue mouth rinse which may be used as a routine procedure after thorough clinical examination to discover undetected lesions.

In the makeup of the rinse composition, a 1% toluidine blue solution containing acetic acid with alcohol was used. 1% by weight was selected as a preferred starting amount. Actually the toluidine blue may be utilized in as low amount as 0.5% and as high as 2%. A maximum pH of about 5 is achieved by the use of acetic acid which is preferred to mineral acids, such as hydrochloric or nitric.

An example of a preferred composition (a weak acid) of this invention is as follows:

Toluidine blue 0 power—1 gram, acetic acid 10 cc.
Absolute alcohol—4.19 cc.
Distilled water—86 cc.

to make up 100 cc. of a 1% solution of toluidine blue. This is adjusted to a pH of 4.5 or less.

It is postulated that the acetic acid and alcohol reduce the mechanical retention of the stain.

A technique for application of the toluidine blue rinse is as follows:

(a) Rinse mouth with 1% acetic acid for 20 second;
(b) Rinse mouth with water for 20 seconds twice;
(c) Rinse mouth with 5 cc. 1% toluidine blue solution, gargling simultaneously;
(d) Rinse mouth with 1% acetic acid (5 oz.) for one minute;
(e) Rinse mouth with water.

The three tables below show the results after 105 lesions which persisted 10–14 days after initial detection were stained and biopsied.

Table I compares pathological diagnosis with toluidine blue application results. Of 51 carcinomas, one stained negative for a false negative rate of 2.0%.

Five of the 54 non-malignant lesions stained either as positive (4) or equivocal (1) for a false positive rate of 9.3%.

Table II compares pathological diagnosis with toluidine blue Rinse A results. Of 51 carcinomas, 3 stained negative, for a false negative rate of 5.9%. Four of the 54 non-malignant lesions stained as positive for a false positive rate of 7.4%.

Table III compares false negative and false positive rates using toluidine blue application and toluidine blue rinse.

TABLE I

| | TOLUIDINE BLUE APPLICATION | | | |
|---|---|---|---|---|
| PATHOLOGICAL DX | Positive | Equivocal | Negative | Total |
| Carcinoma | 37 | — | 1 | 38 |
| Carcinoma-in-Situ | 12 | 1 | — | 13 |
| Atypia | 1 | 1 | 1 | 3 |
| Benign | 3 | — | 48 | 51 |
| TOTAL | | | | 105 |

False negatives = 1/51 = 2.0%. False positives = 5/54 = 9.3%*
*If a pathological diagnosis of atypia is considered "premalignant", the false positive rate would be (3/51) 5.9%.

TABLE II

| | TOLUIDINE BLUE RINSE | | | |
|---|---|---|---|---|
| PATHOLOGICAL DX | Positive | Equivocal | Negative | Total |
| Carcinoma | 34 | 2 | 2 | 38 |
| Carcinoma-in-Situ | 9 | 3 | 1 | 13 |

TABLE II-continued
TOLUIDINE BLUE RINSE

| PATHOLOGICAL DX | Positive | Equivocal | Negative | Total |
|---|---|---|---|---|
| Atypia | 2 | — | 1 | 3 |
| Benign | 2 | — | 49 | 51 |
| TOTAL | | | | 105 |

False Negatives = 3/51 — 5.9%. False positives = 4/54 = 7.4%*

*If a pathological diagnosis of atypia is considered "premalignant", the false positive rate would be (2/51) 3.9%.

TABLE III
COMPARISON OF TOLUIDINE BLUE APPLICATION AND RINSE

|  | False Negatives | False Positives |
|---|---|---|
| Toluidine Blue Application | 2.0% | 9.3% |
| Toluidine Blue Rinse | 5.9% | 7.4% |

COMPARISON OF THE PRESENT RINSE TECHNIQUE WITH APPLICATION

In experimentation, asymptomatic observed lesions were worked with in comparing application and rinse. This technique is for use primarily by those whose clinical acumen in detecting early asymptomatic lesions is limited and therefore many of the lesions that were stained by rinse would not have been observed or picked up by the clinical examination for application. Although the false negatives for rinse were 5.9% as compared to 2.0% for application, the finding of unobserved lesions by rinse in essence increased the false negatives for the application technique. False positives were sightly lower for the rinse technique but essentially of no great moment since it was low for both.

The results from the studies indicate that for the practitioner, the rinse of the present invention has been shown to be effective in picking up lesions not observed. It is expected that, if a lesion is found with the rinse, a 10-14 day waiting period be allowed and then the specific area be re-stained by means of toluidine blue application. If it is positive once again, one must assume that the lesion is carcinoma (in-situ or invasive) unless proven otherwise. It may also be used in a situation where the rinse is utilized on Day 1 and again during the period Day 10 to Day 14.

EXAMPLE I

Examples of rinse techniques tried according to the present invention

Rinse A-Rinse mouth with 1% acetic acid for 20 seconds. Rinse mouth with water for 20 seconds, twice. Rinse mouth with 5 cc. 1% toluidine blue solution, gargling at the same time. Rinse with 1% acetic acid (5 oz.) for one minute. Rinse with water.

Rinse B-Rinse mouth with water for 20 seconds, twice. Rinse mouth well with 1% acetic acid for 20 seconds. Rinse with 5 cc. 1% toluidine blue solution, gargling at the same time. Rinse with 1% acetic acid (5 oz.) for one minute. Rinse with water.

Rinse C-Rinse mouth with water for 20 seconds, twice. Rinse mouth with 5 cc. 1% toluidine blue solution, gargling at the same time. Rinse with 1% acetic acid (5 oz.) for one minute. Rinse with water.

With reference to the rinse techniques of the above example, the following summation is noted. Each rinse was ranked by extent and intensity of color. The ranks were then summed and averaged for each stain for a score that had the highest effectiveness. Rinse stain A ranked the highest and Rinse stains C and B ranked second and third, respectively.

With general regard to the testing, a stain is considered positive for malignancy if an area stained dark blue, either solid or stippled.

A negative stain generally implied no absorption of the stain by a lesion, however, areas of light blue may occasionally appear after staining. This is usually related to mechanical surface retention or inadequate removal of a thin film of toluidine blue by the acetic acid and water rinse.

What I claim is:

1. A method of detecting malignant lesions of the oral cavity by utilizing toluidine blue as a rinse wherein said rinse is an aqueous acetic acid solution containing a 1% toluidine blue solution comprising acetic acid, alcohol and water, and wherein the toluidine blue rinse is used on Day 1 of a clinical regimen and if an area of stain is detected, an application of toluidine blue is performed on the detected area on a day selected from Day 10-14, said regimen employing toluidine blue rinse comprising
   (a) rinsing the mouth of the patient with 1% acetic acid for a period of about 20 seconds followed by a similar rinse with water twice for about 20 seconds;
   (b) rinsing the mouth of the same patient with 5-10 cc. 1% toluidine blue solution while simultaneously gargling; and
   (c) rinsing with 1% acetic acid solution (5 oz.) for about 1 minute followed by a water rinse.

* * * * *